United States Patent [19]

Bullis et al.

[11] 4,456,883

[45] Jun. 26, 1984

[54] METHOD AND APPARATUS FOR INDICATING AN OPERATING CHARACTERISTIC OF AN INTERNAL COMBUSTION ENGINE

[75] Inventors: Robert H. Bullis, Avon; John A. Kimberley, East Granby, both of Conn.; Robert P. Couch, Palm Beach Gardens, Fla.

[73] Assignee: Ambac Industries, Incorporated, Springfield, Mass.

[21] Appl. No.: 432,501

[22] Filed: Oct. 4, 1982

[51] Int. Cl.³ ............................................. G01N 27/62
[52] U.S. Cl. ....................................... 324/464; 73/116; 324/130; 324/459
[58] Field of Search ....................... 324/457, 464, 71.1, 324/130, 458, 459; 123/357; 340/629, 683

[56] References Cited

U.S. PATENT DOCUMENTS

| | | | |
|---|---|---|---|
| 3,038,118 | 6/1962 | Beckett | 324/464 |
| 3,114,877 | 12/1963 | Dunham | 324/71.1 |
| 3,447,071 | 5/1969 | Webb | 324/464 |
| 3,449,667 | 6/1969 | Gourdine | 324/464 |
| 3,586,468 | 6/1971 | Sims et al. | 324/464 |
| 3,956,928 | 5/1976 | Barrera | 73/116 |
| 4,249,131 | 2/1981 | Owen | 324/464 |

*Primary Examiner*—Michael J. Tokar
*Assistant Examiner*—B. J. Kelley
*Attorney, Agent, or Firm*—Stephen A. Schneeberger

[57] ABSTRACT

A method and apparatus are provided for indicating an operating characteristic of a periodically combusting internal combustion engine, such as a diesel engine, having exhaust gas issuing from one or more combustion chambers in a periodic manner through a duct. The particulate in the exhaust gas stream are electrically charged and of the same polarity, and are grouped in packets associated with the periodic combustion in the respective chambers. An electrically conductive, passive electrode, preferably annular in shape, is disposed such that most or all of the exhaust gas flows therethrough so as to electrostatically sense, principally by induced image charge, the passage of the respective packets of charged particles. The electrode is electrically isolated from the duct. Circuitry with the probe converts the sensed induced image charge to a signal containing a series of pulsating components corresponding in time with the respective particle packets and corresponding quantitatively with the charge-quantity of the respective particle packets. An indicating device responds to the pulsating signal and provides an indication of an operating characteristic of the engine.

The electrode is preferably of short axial extent relative to the packet interval to enhance resolution. Structure and circuitry may be provided to minimize soot deposition and/or leakage currents across an insulator between the electrode and duct. In one instance, the indicating device may respond to the root mean square of the pulsating signal to provide a quantitative indication of the level of particulate in the exhaust gas stream. In another instance, the successive pulsations of the signal waveform may be displayed to afford evaluation of the performance of the respective combustion chambers and/or injectors.

21 Claims, 8 Drawing Figures

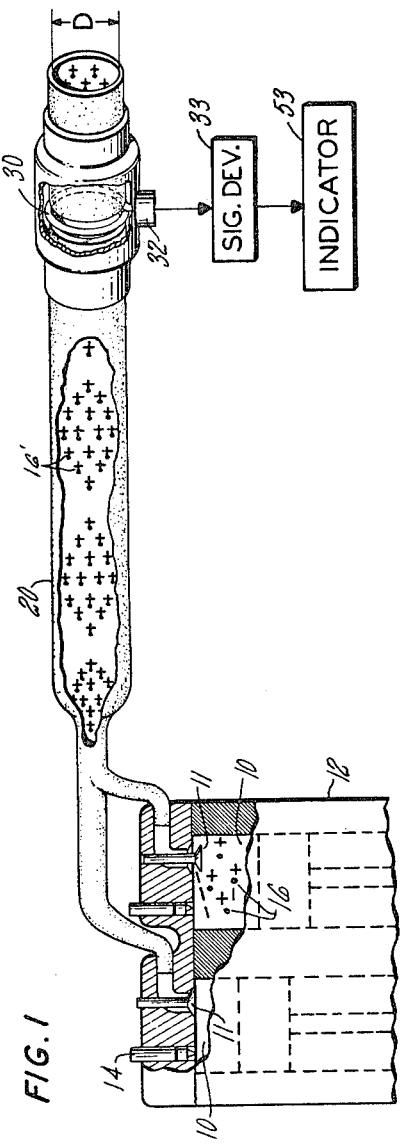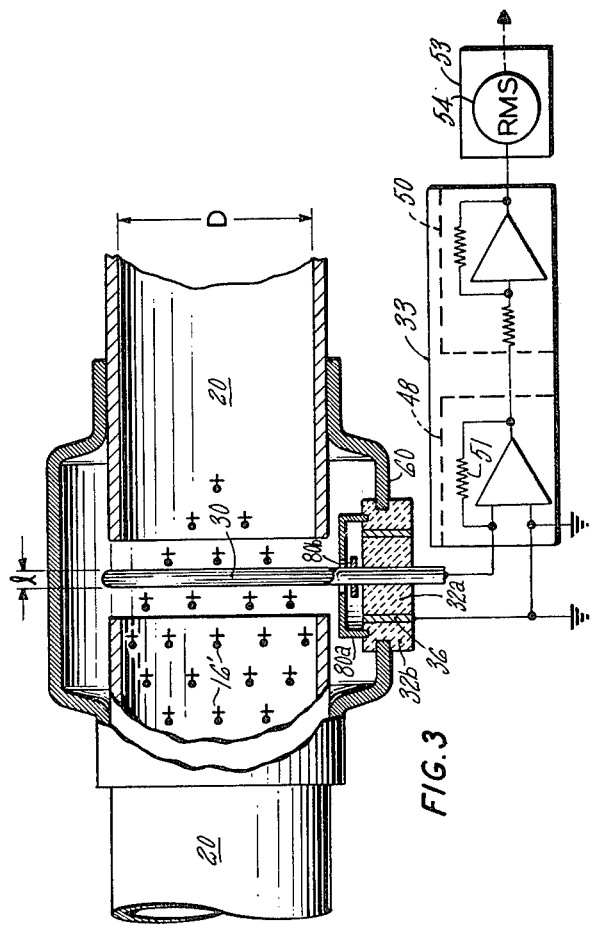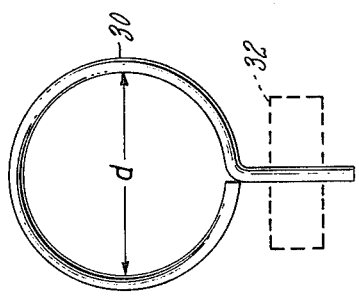

METHOD AND APPARATUS FOR INDICATING AN OPERATING CHARACTERISTIC OF AN INTERNAL COMBUSTION ENGINE

DESCRIPTION

Technical Field

This invention relates to the technique and apparatus for indicating an operating characteristic of an internal combustion engine and more specifically to the method and apparatus for sensing the particulate in the exhaust gas stream issuing in a periodic manner from an internal combustion engine and indicating an operating condition of the engine from the sensed particulate.

Background Art

Interest in maintaining high levels of air quality have focused attention on the importance of reducing emissions from internal combustion engines, and especially the diesel engines which power a variety of on- and off-road vehicles. The manufacturers of such engines and vehicles, as well as those interested in the ongoing and/or periodic monitoring and testing of exhaust gas particulate levels seek accurate, reliable and relatively economical means for accomplishing that end.

The present industry standards for particulate emission measurements are opacity meters, which employ optical techniques and gas filter patch samples. The opacity meter, which provides greater measurement flexibility and continuous measurement capability operates on optical principles which require the provision of a source of light and means for sensing the level of light transmitted through and/or reflected by particles contained in the exhaust gas stream.

Opacity meters, however, require a relatively stable mounting arrangement and frequent cleaning and are not particularly well suited for on-vehicle applications. Moreover, the relatively high cost of opacity meters minimizes their appeal in a large volume market. Lastly, because of the optical characteristics typical of these meters, particle emissions one micron in size and larger have a greater sensitivity to detection than particles below the one micron level. Accordingly, most optical detectors are referred to as smoke meters rather than particulate emissions detectors because of this size discrimination effect which does not present a representative picture of the total exhaust gas particulate emissions.

Instruments have existed for measuring the concentration of particles, i.e. aerosols, in a flowing gas stream utilizing electrostatic techniques. However, these instruments typically establish a high voltage corona in the particle flow path for placing a charge on the flowing particles. Examples of such instruments are illustrated and disclosed in U.S. Pat. No. 3,526,828 issued Sept. 1, 1970 to K. T. Whitby for Method and Apparatus for Measuring Particle Concentration and in U.S. Pat. No. 3,114,877 issued Dec. 17, 1963 to S. B. Dunham for Particle Detector Having Improved Unipolar Charging Structure. In U.S. Pat. No. 3,359,796 issued Dec. 26, 1967 to R. C. Dimick for Apparatus for Measuring Mass Flow Using a Shielded Probe, an instrument is disclosed which measures the mass flow of charged solid particles entrained in a flowing gas stream, which particle charges are acquired by frictional contact with the wall of the conduit. Impact of the charged particles with a sensor element creates a small electrical current which is used as a measure of the particle mass flow. Operation of this device is limited to situations where frictional charging is the principal charging process and where flow velocities are low enough for impact charge collection to overcome gas dynamics. Thus, no consideration is given to using that device for measuring the emission level of particulates in the exhaust from an internal combustion engine.

In U.S. Pat. No. 3,470,551 issued Sept. 30, 1969 to A. A. Jaffe et al for Fire and Smoke Detector, there is disclosed a device for detecting the existence of fire and smoke by sensing the net electrical charge associated with particles resulting from combustion. This device requires a field-free region for operation. Moreover, it is limited to two-state operation, i.e. "smoke" or "no-smoke" and is not intended to measure differing particulate levels of the exhaust gas stream issuing from an internal combustion engine.

A smoke measuring device for the exhaust gases from internal combustion engines is described in U.S. Pat. No. 3,744,461 issued July 10, 1973 to J. D. Davis for Method and Apparatus for Reducing Exhaust Smoke in Internal Combustion Engines. That smoke measuring device utilizes the principle that carbon particles in the exhaust gas stream issuing from an internal combustion engine are electrically charged. An electrode is placed in the exhaust gas stream, the charges are collected at the electrode by impaction, and electrical circuitry provides an output signal corresponding to the potential developed between the electrode and the exhaust duct, which signal may, in highly selective cases such as low flow velocity, be indicative of a smoke density level and may be used to control the quantity of fuel delivered to the engine.

The smoke measuring device of the aforementioned Davis patent, while providing some measure of the particulate level in an engine exhaust gas stream, also exhibits certain limitations. By relying on charge collection by impaction, the electrode must have a relatively large surface area in and/or adjacent to the gas stream and requires a significant electrical potential to overcome gas dynamic flow stream forces. Further, the impaction process can significantly shorten the life of the electrode by erosion. Additionally, because of the large extent of the electrode in the direction of gas flow, the resulting signal is generally representative of an average of the discrete exhaust outputs of several cylinders.

Although several factors may contribute to excessive smoke or particulate emissions from internal combustion engines, one factor may be the improper operation of a fuel injector in a particular cylinder. Moreover, such defective operation of the fuel injector may degrade the engine's performance and thereby adversely affect fuel economy.

It is therefore, a principal object of the present invention to provide an improved apparatus for indicating an operating characteristic of a periodically combusting internal combustion engine by sensing the particulate emissions in the exhaust gas stream issuing from the engine and deriving the indication therefrom.

It is a further object of the invention to provide a particulate sensor which is relatively durable, long lived and is suited for continuous on-vehicle application.

It is yet a further object of the invention to provide an improved apparatus for sensing and indicating quantitatively the level of particulate in an exhaust gas stream issuing in a periodic manner from an internal combustion engine.

It is a still further object of the present invention to provide a method and apparatus for sensing and indicating the relative performance of fuel injectors in a multi-injector/multi-cylinder engine based on the particular emission characteristics of the respective cylinders.

Disclosure of the Invention

According to the present invention, there is provided a technique and apparatus for indicating an operating characteristic of a periodically combusting internal combustion engine, which engine has one or more combustion chambers and an exhaust gas stream issuing in a periodic manner through ducting from the combustion chambers. The exhaust gas stream contains electrically charged particles of the same polarity at a monitoring location downstream of the engine combustion chambers, and the engine's periodic discharge of exhaust gas from respective cylinders causes the charged particles to be grouped in packets. An electrically conductive passive electrode, preferably of annular configuration, is disposed in proximity with the exhaust gas stream at the monitoring location to electrostatically sense, principally by means of an induced image charge, the passage of the respective packets of charged particles. The electrode is electrically isolated from the exhaust duct and is preferably configured and/or positioned to minimize any blockage of the flow of exhaust gas. Signal developing circuitry is connected to the sensing electrode for providing an electrical signal in response to the sensed passage of the particle packets. That signal contains a series of distinct pulsating components corresponding in time with the passage of the respective said particle packets and corresponding quantitatively with the charge-quantity of the respective particle packets. An indicating device receives these pulsating signals as its input and provides therefrom an indication of an operating characteristic of the engine.

In a preferred embodiment the sensing electrode is an electrically conductive closed annulus or loop positioned in proximate coaxial relation with the exhaust gas stream and which preferably has an axial extent which is short relative to spacial dimension of successive particle packets. The electrode may be incorporated in the exhaust gas duct or pipe, or it may be located a short distance beyond the downstream end thereof. The diameter of the annular electrode is sufficiently large to enable a substantial portion or all of the exhaust gas stream to pass therethrough and may typically approach or exceed the diameter of the exhaust gas duct. Because the sensing electrode either is in, or is in close proximity with, the exhaust gas stream, it may be desirable to provide a guard ring for the conduction of leakage currents and/or a shadow shield to minimize the accumulation of soot on an insulating surface which supports the electrode.

Signal developing circuitry is connected to the electrode such that a pulsating signal is developed thereby in response to the passage of respective charged particle packets through or otherwise past the sensing electrode. The resulting pulsating signal corresponds in time with the passage of the respective charged particle packets and corresponds quantitatively with the charged particles in a respective packet. Due to considerations of Gauss' Law, the annular probe configuration provides equal weighting of each particle passing through the annulus independent of radial charge density distribution.

A device responsive to at least the pulsating components of the developed signal provides therefrom an indication of an operating characteristic of the engine. In one embodiment, the device may respond to the root mean square of the pulsating signal to provide a quantitative indication of the level of particulate in the exhaust gas stream. In another embodiment the device may comprise a cathode ray tube or the like for displaying the successive pulsations of the signal waveform to afford evaluation of the performance of the respective individual cylinders and/or fuel injectors. In this latter regard, correlation of a particular displayed signal with operation of a specific injector may be accomplished by perturbing the operation of the particular injector and noting such change in the display of a particular signal in the sequence of signals corresponding to successive injectors. Such correlation of a particular displayed signal with a particular injector might also be calculated automatically as a function of system geometry and present operating conditions.

Brief Description of the Drawings

FIG. 1 is a diagrammatic view of an internal combustion engine having the electrostatic induction particulate sensor installed in the exhaust stream thereof and providing a pulsating signal to circuitry for indicating an operating characteristic of the engine;

FIG. 2 is a view of a preferred form of the electrostatic induction particulate-sensing probe viewed in the direction of exhaust gas flow;

FIG. 3 is a view of the probe of FIG. 2 perpendicular to the gas flow, including a mounting arrangement and illustrating the signal developing and utilizing circuitry in greater detail;

Figure 4:
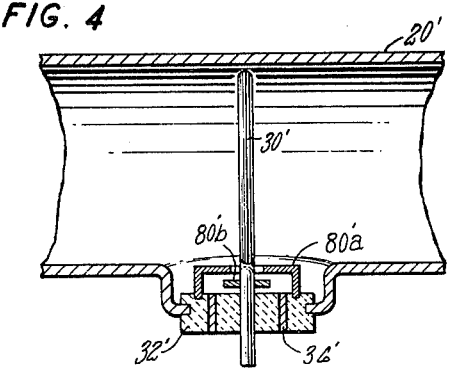
FIG. 4 is another mounting arrangement for a probe in accordance with the invention.

Best Mode for Carrying Out the Invention

Referring to FIG. 1 there is depicted within one of the combustion chambers 10 of a multi-cylinder internal combustion engine, such as compression ignition engine 12, the ionization which results from the combustion process. This phenomenon, in which the gas in the immediate combustion region becomes electrically conducting, is the well known principle upon which flame ionization and combustion detectors are based. In the operation of internal combustion engines, and especially compression ignition or diesel engines, various particulates 16 are produced as a result of incomplete combustion. These particulates may vary in size and composition, and encompass a wide distribution, including many less than one micron in size. Since these particles 16 are produced within the individual cylinders of the engine, they provide sites upon which free charges resulting from the combustion process can attach. As is usual with attachment or clustering reactions taking place at atmospheric pressures or above, charge selection occurs, i.e. only positive or only negative charge species ultimately reside on the finely divided particles 16.

For purposes of illustration in FIG. 1, the particles 16 are shown to have acquired a positive charge as they begin movement away from the combustion chamber through the exhaust. Subsequent to the charge attachment process which takes place in combustion chamber 10, charge separation results as a consequence of the particles 16 being dominated by gas path flow forces, whereas the unattached charges, i.e. negative charges in FIG. 1, which have significantly greater mobilities because of their much smaller masses, are dominated by electrostatic forces. Accordingly, a rapid loss of these lighter (negative) particles to the walls of the cylinder and associated manifold results. The degree to which this charge separation occurs is a function of the concentration of the particles 16 produced in each individual cylinder as a result of the incomplete combustion taking place. Specifically, the greater the formation of particles, the greater will be the attachment of one charge thereto and the separation therefrom of the other charge. Accordingly, determination of the quantity of charge provides a direct measure of the level of particulate in the engine exhaust gas stream.

It has been demonstrated that once charge-separated, these charged particles, designated 16' in FIG. 1, passed directly through the engine exhaust system to the outside atmosphere. Important to the present invention in which the engine 12 is of the type which periodically combusts its fuel in one or more combustion chambers and then discharges its exhaust in periodic pulses, as by valving 11 or the like, it has also been found that the packet of charged particles resulting from the exhaust discharge of an individual cylinder passes relatively unimpeded through even the exhaust staging of a turbocharger. This occurs primarily because flow forces dominate over electrostatic forces under typical engine operating conditions. Moreover, the packet of particles from each particular cylinder remains relatively intact and separate from those of each of the other cylinders, as in the form of discrete pulses. These packets of charged particles are represented by dense groups of charged particles 16' in FIG. 1.

The detection of the charged particles 16' in the exhaust duct, or pipe, 20 of engine 12 is accomplished by use of an electrically passive electrostatic induction probe or electrode 30 mounted downstream of the combustion chambers 10 in operative proximity with the exhaust gas stream. The term "electrically passive" as used herein means the probe does not operate on an impaction or charge collection principle, and thus requires little or no biasing potential for signal generation, although some bias may be used in conjunction with a guard ring as described hereinafter. The probe 30 might be mounted in an extension conduit associated with a test stand for connection with the exhaust pipe 20 of engine 12 to test or diagnose the engine. In another application, the probe 30 may be mounted directly in the exhaust system of an engine for on-vehicle use. An insulator 32 provides electrical isolation from pipe 20.

The key to providing a truly representative measure of the passage of particles 16' in the exhaust resides in the fact that relatively little or none of the actual charge on the particles is collected by the probe. Rather, the passage of substantially all of the charged particles is detected because an image charge of opposite sign is induced in the conducting probe electrode 30 as a charged particle approaches the vicinity of the probe surface. This results in a real electrical current flow through signal developing circuitry 33 connected to probe electrode 30, as will be hereinafter described. By virtue of the induced image charge phenomenon, as the charged particle recedes in the flow away from electrode 30, the magnitude of the induced charge on that electrode surface decreases, resulting in a current flow in the opposite direction. Accordingly, although a small alternating current flow would be derived from the passage of a single charged particle 16', in the normal instance a much larger-magnitude signal results from the passage of a packet, or puff, of particles from the exhaust gas discharge of an individual cylinder.

For the purpose of comparing the performance of individual cylinders within a given engine, a time-resolved measurement or analysis of the signal, and specifically the AC-like pulsating signal induced in probe 30 by the passage of the exhaust gas puffs from the individual cylinders of the engine, provides this information directly. The charge induced in electrode 30, and thus current in the signal circuitry, is a function of the number or quantity of charged particles 16 passing the electrode in the exhaust gas stream at the particular moment. An increase in particle concentration during respective exhaust gas puffs is manifested by an increase in the magnitude of the charge induced in electrode 30 and thus an increase in the voltage or current signal developed therefrom.

Referring to FIGS. 2 and 3, a preferred embodiment of electrostatic particle-detecting probe 30 is illustrated in greater detail. Probe 30 comprises an annular electrode formed of electrically conducting wire and oriented such that its axis is parallel to, and preferably substantially coaxial with, the axis or centerline of the exhaust gas flow in the tubular pipe 20. It will be understood that the conductive probe 30 may have an insulating covering without impeding its performance in the present invention. In FIG. 3, the electrode 30 is shown mounted in and supported by ceramic insulator structure 32 which is in turn suitably mounted and sealed in an annular collar 60 which sealingly connects adjacent ends of pipe 20 at a break formed therein at a monitoring location.

In accordance with the invention, the length, l, of the electrode 30 axially of the gas flow is limited in order to obtain good signal resolution between successive packets of charged particles. It will be appreciated that as the number of combustion events per unit of time increases, the interval or length between successive particle packets decreases. Therefore, the length, l, of electrode 30 should be sufficiently short that at any instant it is sensing or responding to the charged particles of substantially only one packet, or preferably only an incremental portion thereof. The interval or spacing between charged particle maxima in successive packets will, for a representative system, largely be a function of the number of engine cylinders, the engine's operating displacement, the speed of the engine and the geometry of the exhaust ducting system. Typically, in a four cylinder diesel engine system capable of operating to 5,000 rpm, an electrode length, l, of about 3–4 mm has given good results. For such a system, the length, l, of the electrode 30 should generally be less than about 10–15 mm, which is much less than the typical diameter D of exhaust duct 20 thereat, i.e. 50 mm.

The electrode 30 is preferably affected by substantially all of the charged particles in a packet, rather than by a relative few nearest the electrode. Thus, because of considerations of Gauss' Law, an annular probe configuration is preferred, and a preferred electrode diameter, d, is one which is sufficiently large to allow substantially all of the exhaust gas stream in duct 20 to pass therethrough. The electrode diameter, d, preferably is near or exceeds the duct diameter. In the FIG. 3 embodiment, the diameter, d, of electrode 30 somewhat exceeds duct diameter, D, so that the entire gas stream flows therethrough and no flow blockage occurs. Typically, the radial thickness of an electrode 30 is only about 1–4 mm to minimize its surface area transverse to the flowing gas so as to minimize any flow blockage, particularly if it is positioned in the gas stream.

Figure 5:
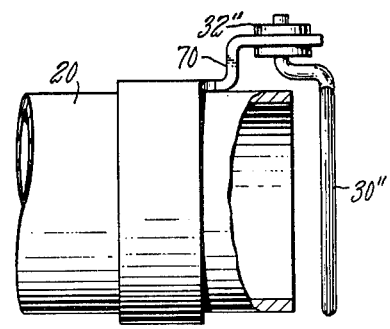
FIG. 5 is a further mounting arrangement for a probe in accordance with the invention.

Referring briefly to FIGS. 4 and 5, there are illustrated alternative mounting arrangements for the electrostatic probe. In FIG. 4 the electrode 30' is also of annular form and insulated from pipe 20 by an insulator 32' which is sealingly installed directly in an opening in the wall of pipe 20. It will be noted that the diameter, d, of probe 30' is near, but slightly less than, the diameter, D, of pipe 20 so as to be in spaced (and thus insulated) relation with the pipe. It will be noted that substantially all of the exhaust gas stream and entrained particulates pass through this probe and provide a signal having the requisite properties, although this configuration does possess the limitations of increased restriction of the flow path and exposure to soot deposition.

The electrode 30" of FIG. 5 may also be annular, and is mounted in an insulator 32" which is supported by a bracket 70 mounted near the end of exhaust pipe 20. The electrode 30" may be located axially at or just beyond the end of pipe 20 such that the insulator 32" need not be mounted with a gas-tight seal. Moreover, the insulator 32" may be positioned upstream of the end of pipe 20, to minimize or eliminate soot accumulation thereon. In yet another possible embodiment (not shown), the probe electrode might be embedded in an annular insulator, which insulator might be inserted into the exhaust duct or form an extension thereto However, in such instance care must be taken to avoid build-up of soot or other conductive deposits on the insulator.

A high degree of electrical isolation between probe 30 and the conductive portions of the duct 20 must be maintained. If the insulator 32 is positioned such that it is exposed to the exhaust gas stream, the potential for soot accumulation on it exists, which may in turn give rise to leakage currents, particularly when damp. To minimize soot accumulation, one, or possibly two shadow shields 80$_a$ and 80$_b$ in FIG. 3 or 80'$_a$ and 80'$_b$ in FIG. 4, may be arranged to shadow the surface of the insulator from the direct gas flow.

Whether or not shadow shields are employed, leakage currents involving the probe electrode may be minimized through use of a guard ring. Accordingly, the insulator 32 in FIG. 3 and the insulator 32' in FIG. 4 include guard rings 36, 36' respectively. Insulator 32 is comprised of an inner cylindrical insulator 32$a$ and a radially outer cylindrical insulator 32$b$ concentric with insulator 32$a$. The base of annular electrode 30 is fixedly mounted, as by a friction fit or bonding, into inner insulator 32$a$. The insulator 32 also includes a conductive metal guard ring 36 intermediate and affixed to the inner and outer insulators 32$a$, 32$b$ respectively. Guard ring 36 is cylindrical and is concentric with insulators 32$a$, 32$b$ and the portion of probe 30 extending therethrough. The guard ring 36 is operated at substantially the same potential as the probe electrode 30, thus forming a region within and across the surface of the ceramic which is at substantially the same potential as the electrode 30. Accordingly, no leakage current can flow across this region. Leakage currents from the surrounding structure of engine 12 and exhaust duct 20 can pass over the outer insulator 32$b$, via the soot, to the guard ring 36. From the guard ring 36, these leakage currents are shunted to ground and therefore do not arrive at the probe electrode 30. Further, since the electrode 30 and the guard ring 36 are maintained at substantially the same potential, no leakage of currents occurs between the guard and the electrode.

Signal developing circuitry 33 is connected in the circuit of probe 30 between the probe and the ground reference potential. Signal developing circuitry 33 includes a current-to-voltage converter 48 and a gain circuit 50. Assuming a 1 megohm resistor 51 across converter 48, a 1 microampere input provides a 1 volt output. Gain circuit 50 may typically have a gain factor of fifty.

In the embodiment illustrated in FIG. 3, the indicator 53 consists of a root mean square (rms) volt meter 54 which is connected to the output of signal developing circuitry 33 to receive the signal voltage as its input.

The output of the rms meter 54 may be a visual indication of the root mean square value of the signal occasioned by the passage of successive charged particle packets through the exhaust duct 20. This indication may be calibrated and expressed in terms of the percentage of particulate in the exhaust gas stream or it may be referenced to opacity measurements and expressed as a change in opacity in the gas stream. Alternatively or additionally, with the appropriate time constants applied to the signal-averaging circuitry a substantially DC electrical signal indicative of the average value of particulate in the exhaust gas stream may be provided. Those time constants may be provided as function of engine combustion frequency. Such an indicating signal may additionally or alternatively be used for various control purposes.

The indicating device 53 might alternatively comprise a cathode ray tube (CRT) or similar display device for displaying the output signal from circuitry 33 in a time-resolved manner. More specifically, the signal provided by circuitry 33 may comprise the vertical, or Y, input to an X–Y display in which time is measured along the X axis. In other words, the pulsations appearing across resistor 50 as a result of the passage of successive particulate packets in the exhaust gas stream are displayed in a similar time-resolved succession on the face of a display device, as in FIGS. 6, 7 and 8.

Figure 6:
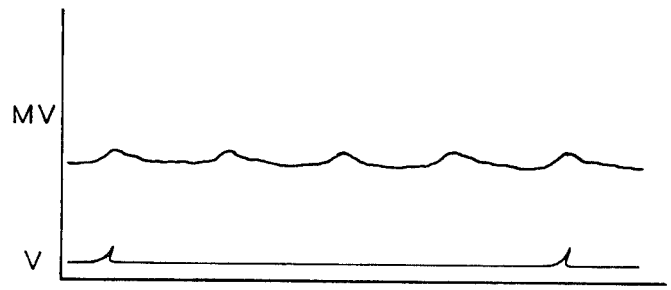
FIG. 6 is a display of the sensed signal for relatively low-level particulate packets in the exhaust.
Figure 7:
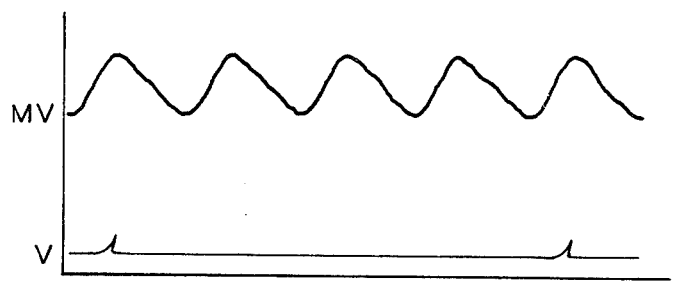
FIG. 7 is a display of the sensed signal for relatively higher level particulate packets in the exhaust.
Figure 8:
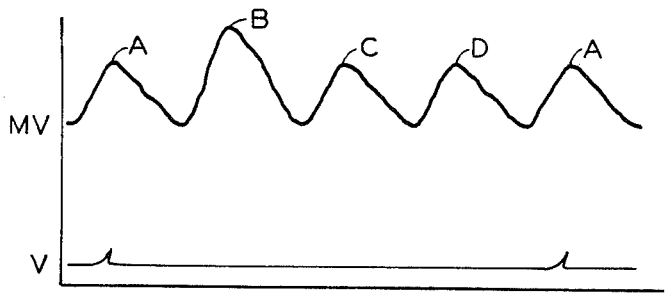
FIG. 8 is a display of the sensed signal for differing particulate levels in successive particulate packets from respective successive combustion chambers.

The signal displays of FIGS. 6, 7 and 8 were obtained at a common engine speed and were provided by connecting the output from the probe 30 directly to the one megohm impedance at the "Y" input of a Tektronics 7834 oscilloscope. These displays are depicted as the upper trace in each of the FIGS. 6, 7 and 8. A lower trace is also contained in each of those Figs. for illustrating timing signals developed, as for instance, from, and coinciding with, each second top dead center (TDC) event associated with a particular one of the engine cylinders. The TDC signal may be provided in a known manner, as by a magnetic sensor (not shown) detecting a timing mark on the engine flywheel and suppressing the unwanted indication of each second TDC event. Although those timing signals are shown in time coincidence with the peak in the particulate signals, it will be understood that such is normally not the case because of the delay interval between combustion chambers and the position in the exhaust gas stream at which probe 30 is stationed, i.e. phase lag. The upper and lower traces are preferably triggered by some periodically recurring event in the engine operating cycle, as by the TDC signal constituting the illustrated timing signals mentioned above, such that the trace pulsations appear relatively stationary. The peaks of the particulate signal on the upper trace have a magnitude of approximately 200 millivolts and typically represent a current level of several tenths of a microampere. The particulate signals in FIG. 6 resulted for exhaust gas conditions coinciding with measured opacity levels below about 1%.

FIG. 7 is an illustration similar to FIG. 6 with the only difference being that the particulate-level signals are of substantially greater magnitude than those of FIG. 6 and are correspondingly representative of a higher particulate level, i.e. coinciding with measured opacity levels of about 13%. Indeed, the magnitudes of the particulate level signals and measurements from an exhaust dilution tunnel exhibit good correlation across a broad range of particulate levels.

FIG. 8 depicts a display of a type similar to that of FIGS. 6 and 7, however, it illustrates a difference in the relative particulate levels in the exhaust gas puffs issuing from different combustion chambers. Specifically, the magnitudes of the particulate level signals or pulses A, C and D from the first, third and fourth cylinders (not all shown) in a four cylinder firing sequence are of relatively normal magnitude, whereas the magnitude of the signal B associated with the second cylinder in the sequence is of substantially greater magnitude. By correlating the successive particulate signals with the respective engine cylinders from which they derive, it is possible to identify the cylinder and combustion chamber in which an abnormal particulate level condition arises. Such conditions are generally caused by need for adjustment or repair of a particular one of the fuel injectors 14 and the identification of the offending injector is facilitated by this capability.

Correlation of a particulate packet signal with a particular cylinder and/or injector may be accomplished by "perturbing" the injector such that the "perturbance" appears in the particulate signal, then noting its location in the sequence of particulate signal pulses and referencing the other pulses of predetermined firing or combustion sequence thereto. An injector's operation may be "perturbed" by breaking the fuel line to it or by rotating its holder. Such technique is particularly suitable for identifying which of a plurality of injectors may be operating in an abnormal manner and is conveniently performed by repair and service personnel as well as by manufacturing personnel during the original checkout of the engine. It will be understood that in addition to identifying which cylinder and/or injector is malperforming, some indication as to the nature of that malperformance may also be gained. For instance, the magnitude of the particulate signal may be indicative of an excess or a shortage of fuel supplied by a particular injector.

It will be understood that the need to perturb an injector to identify its location in a sequence of displayed particulate pulses may be avoided if it is otherwise possible to determine the transport time between any displayed particulate pulse and the combustion chamber from which it issued. Factors such as exhaust system geometry, engine speed engine operating event (i.e. TDC), engine and/or air temperature, air pressure, etc. would typically be included in such a determination.

As an alternative or supplement to the rms meter 54, the signal provided by probe 30 might be sampled at a relatively high frequency and the samples then averaged to provide a measure of the particulate level.

The probe of the invention is preferably a loop, although other probes may be used. The probe need not be short-circuited on itself (as in FIG. 2), or it may be shorted, as shown in a commonly owned copending U.S. patent application Ser. No. 432,507 entitled Noncontact Electrostatic Hoop Probe for Combustion Engines filed contemporaneously herewith by R. P. Couch. The probe preferably has little or no electrical contact with the gas stream as described hereinbefore, and thus may take the forms described herein. Alternatively, it may be totally electrically insulated from the gas stream by virtue of electrical insulation or size, as shown in the aforementioned application of R. P. Couch.

Although this invention has been shown and described with respect to detailed embodiments thereof, it will be understood by those skilled in the art that various changes in form and detail thereof may be made without departing from the spirit and scope of the claimed invention. For instance, if the insulator which isolates the probe from the exhaust pipe is sufficiently removed from contact with the exhaust gas, there may be no need for shadow shields and/or guard rings. Moreover, although the fully annular electrode configuration provides certain advantages, it will be understood that the probe might be formed of one or more arcuate electrodes each extending but a portion of a full circle and electrically connected to one another. Moreover, the electrode might be linear and extend into or near the gas stream transverse to its direction of flow. As previously stated, such electrodes will have a relatively small dimension, l, in the direction of gas flow, but are somewhat more dependent upon the radial location of charged particles in the exhaust gas stream that were the aforedescribed annular probes.

Having thus described a typical embodiment of our invention, that which is claimed as new and desired to secure by Letters Patent of the United States is:

1. Apparatus for indicating an operating characteristic of a periodically combusting internal combustion engine having duct means defining an exhaust gas path, said engine having an exhaust gas stream issuing in said path in a periodic manner from at least one combustion chamber of the engine, said exhaust gas stream containing electrically-charged particles, said charge being of the same polarity on substantially all of the charged particles at a monitoring location along said path, and said periodic combustion and issuance of exhaust gas causing said charged particles to be grouped in respective periodic packets, said apparatus comprising:

electrically conductive, passive electrode means inductively responsive to electrically-charged particles passing thereby, said electrode means being disposed in proximity with said exhaust gas stream at the monitoring locating in electrical isolation from said duct means for sensing, principally by the induced image charge, the passage and the charge-quantity of the respective packets of charged particles;

means operatively connected to said electrode means and responsive to the sensed passage and charge-quantity of the particle packets for providing an electrical signal having a series of distinct pulsating components corresponding in time with the passage of respective one of said particle packets and corresponding quantitatively with the charge-quantity of the respective ones of said particle packets; and means responsive to at least said pulsating components of said signal for indicating an operating characteristic of the engine.

2. The apparatus of claim 1 wherein the interval between successive packets of charged particles always exceeds a certain distance over the full operating range of the engine and wherein the length of said electrode axially of said exhaust gas stream is less than said certain distance thereby to provide sufficient resolution to detect successive individual charged-particle packets.

3. The apparatus of claim 2 wherein said length of the electrode axially of the exhaust gas stream is substantially less than said certain distance.

4. The apparatus of claim 1 wherein said electrode is substantially annular and the axis of the annulus is substantially parallel to the axis of the exhaust gas stream thereat.

5. The apparatus of claim 3 wherein said electrode is substantially annular and coaxial with the exhaust gas stream thereat.

6. The apparatus of claim 5 wherein the inside diameter of said annular electrode is sufficient to enable the majority of the exhaust gas stream thereat to flow therethrough.

7. The apparatus of claim 6 wherein the inside diameter of said annular electrode is at least as large as the gas stream thereat.

8. The apparatus of claim 5 wherein said electrode is mounted in and extends from an insulator, said insulator including a surface in communication with said exhaust gas stream, and including a conductive guard element disposed in said insulator surface, said guard element encircling and being spaced from said electrode for providing a preferential conductive path for leakage currents occasioned in any soot deposits on said surface of the insulator.

9. The apparatus of claim 8 wherein said guard element and said electrode are each connected substantially independently of one another to substantially the same potential.

10. The apparatus of claim 9 wherein said guard element and said electrode are each connected to substantially ground potential.

11. The apparatus of claim 9 further including shadow-shielding means interposed between said exhaust gas stream and said flow-contacting surface of said insulator to impede the deposition of soot onto the flow-contacting insulator surface from the exhaust gas stream.

12. The apparatus of claim 1 wherein said engine characteristic indicating means comprises circuit means for providing an output signal corresponding to the particulate emission level of each respective cylinder.

13. The apparatus of claim 1 wherein said engine characteristic indicating means comprises circuit means for providing an output signal corresponding to the root mean square of the pulsating signal and thereby being indicative of the level of particulate in the exhaust gas stream.

14. The apparatus of claim 1 wherein said engine characteristic indicating means comprises means for visually displaying the waveform of said signal including said pulsating components to afford visual analysis thereof.

15. The apparatus of claim 5 wherein the engine is a multicylinder compression-ignition engine and said engine characteristic indicating means comprises means for visually displaying the waveform of said signal including said pulsating components for a plurality of successive charged particle packets to afford visual comparative analysis thereof.

16. The method of analyzing the relative performance of a fuel injector associated with a respective combustion chamber in a diesel engine, said engine having duct means defining an exhaust gas path and an exhaust gas stream issuing in said path in a periodic manner from said combustion chamber, said exhaust gas stream containing electrically-charged particles, said charge being of the same polarity on substantially all of the charged particles at a monitoring location along said path, and said periodic combustion and issuance of exhaust gas causing said charged particles to be grouped in respective periodic packets, the method comprising:

electrostatically sensing at the monitoring location, principally by the induced image charge, the passage and the charge-quantity of the respective packets of charged particles;

developing an electrical signal from the sensed passage and charge-quantity of each of said charged particle packets said signal having a series of distinct pulsating components corresponding in time with said sensed passage of the respective said particle packets and corresponding quantitatively with the charge-quantity of the respective said particle packets; and indicating an operating characteristic of the engine from the pulsating components of the developed signal.

17. The method of claim 16 wherein the indicated engine operating characteristic is the particulate emission level.

18. The method of claim 16 wherein said step of indicating an operating characteristic of the engine comprises displaying the waveform of the developed signal to afford visual analysis thereof.

19. The method of claim 16 wherein the step of sensing the passage of charged particle packets comprises sensing the passage of charged particles of effectively less than one packet thereof at any instant such that said signal waveform provides good resolution of each said particle packet.

20. The method of claim 19 wherein the step of sensing the passage of less than one packet of particles at any instant comprises positioning an electrically conductive, passive annular electrode in proximate substantially coaxial relation with the exhaust gas stream in electrical isolation from said duct means, the axial length of the electrode being substantially less than the distance between successive packets of charged particles.

21. The method of claim 18 wherein the engine is multi-cylindered, each cylinder having a respective injector, the displayed waveform including at any one time the respective pulsating components corresponding with the particle packets from all of the cylinders in the order of their occurrence, and including the further step of:

perturbing the operation of a predetermined injector sufficiently to cause a noticeable change in one pulse component of the displayed series thereby to identify which of said waveform pulse components corresponds with said predetermined injector.

* * * * *

UNITED STATES PATENT AND TRADEMARK OFFICE
CERTIFICATE OF CORRECTION

PATENT NO. : 4,456,883

DATED : June 26, 1984

INVENTOR(S) : Robert H. Bullis et al

It is certified that error appears in the above-identified patent and that said Letters Patent is hereby corrected as shown below:

Claim 1, line 61: after "monitoring" change "locating" to "location"

Signed and Sealed this

Twenty-third Day of December, 1986

Attest:

DONALD J. QUIGG

Attesting Officer    Commissioner of Patents and Trademarks